US00PP34607P3

(12) United States Plant Patent
Hay et al.

(10) Patent No.: US PP34,607 P3
(45) Date of Patent: Sep. 20, 2022

(54) ***ASPARAGOPSIS* ALGAE NAMED 'BROMINATA'**

(50) Latin Name: *Asparagopsis taxiformis*
Varietal Denomination: Brominata

(71) Applicant: BLUE OCEAN BARNS, Redwood City, CA (US)

(72) Inventors: Vivienne Hay, Redwood City, CA (US); Matthew Rothe, Stanford, CA (US); Joan Salwen, Redwood City, CA (US); Jennifer Smith, San Diego, CA (US); Gal Dishon, San Diego, CA (US); Hannah Resetarits, Salt Lake City, UT (US)

(73) Assignee: BLUE OCEAN BARNS, Kailua-Kona, HI (US)

( * ) Notice: Subject to any disclaimer, the term of this patent is extended or adjusted under 35 U.S.C. 154(b) by 0 days.

(21) Appl. No.: 17/102,287

(22) Filed: Nov. 23, 2020

(65) Prior Publication Data

US 2022/0167540 P1 May 26, 2022

(51) Int. Cl.
*A01H 5/00* (2018.01)
*A01H 13/00* (2006.01)

(52) U.S. Cl.
USPC ..... Plt./395
CPC ..... *A01H 13/00* (2013.01)

(58) Field of Classification Search
USPC ..... Plt./395
See application file for complete search history.

(56) References Cited

U.S. PATENT DOCUMENTS

PP21,091 P3 * 6/2010 Nonomura ..... C12N 1/125 Plt./395
PP23,858 P3 * 8/2013 Biel ..... C12N 1/125 Plt./395

OTHER PUBLICATIONS

Magnusson et al. Sep. 10, 2020. Using oil immersion to deliver a naturally-derived, stable bromoform product from the red seaweed *Asparagopsis taxiformis*. Elsevier: Algal Research 51: 1-7. (Year: 2020).*
Turland, N. J., et al. (eds.) 2018: International Code of Nomenclature for algae, fungi, and plants. (Year: 2018).*

* cited by examiner

*Primary Examiner* — Karen M Redden
(74) *Attorney, Agent, or Firm* — BCF LLP

(57) ABSTRACT

A novel and distinct variety of *Asparagopsis taxiformis*, provided as a source of halogenated compounds.

13 Drawing Sheets

Latin name of genus and species of plant claimed: *Asparagopsis taxiformis.*

Varietal denomination: 'Brominata'.

BACKGROUND INFORMATION

The present invention is a novel and distinct variety of *Asparagopsis taxiformis*, namely 'Brominata' provided as a source of halogenated compounds to inhibit methanogenesis in animals (e.g., ruminant animals).

Methanogenesis (i.e., the production of methane by ruminant animals) is a major contributor to global greenhouse gas emissions. Scientific literature has demonstrated reductions in methane ($CH_4$) production of beef cattle and dairy cows when halogenated compounds are fed as part of the diet. See for example Roque et al., 2020: "Some haloalkanes are structural analogs of $CH_4$ and therefore competitively inhibit the methyl transfer reactions that are necessary in $CH_4$ biosynthesis. The $CH_4$ analogues include bromochloromethane (BCM), bromoform and chloroform and have been proven to be the most effective feed additives for reducing $CH_4$ production".

There are two potential sources for halogenated compounds: artificial synthesis and natural production. Naturally synthesized bromoform, notably in *Asparagopsis* spp. has been found to mitigate a greater percentage of methane gas than synthetic halogenated $CH_4$ analogs at equivalent concentrations in vitro (Machado et. al. 2018), and to maintain the reductions over a 147-day period in vivo (Roque, 2020).

Despite its efficacy, the potential of wild type *Asparagopsis taxiformis* (also referred to herein as AT) as a feed additive to inhibit methanogenesis in ruminant animals is constrained by several factors. These include its unpleasant odor, high iodine content, epiphytic nature, and the lack of capacity, especially in male *Asparagopsis taxiformis* specimens, to synthesize material concentrations of the bioactive halogenated compounds.

This present invention overcomes at least some of those challenges observed with the parent plant and optimizes the plant to synthesize bromoform. In particular, the parent plants (*Asparagopsis taxiformis* gametophytes) come in male and female varieties. It is only the female varieties that synthesize more than nominal amounts of bromoform, meaning that fifty (50%) percent of biomass is not meaningly contributing to the overall production efficiency. With the present invention, not only is one hundred (100%) percent of the biomass synthesizing bromoform, thereby almost doubling production efficiency, but the biomass of the present invention itself accumulates higher levels of bromoform than previously attainable with female gametophytes. Further benefits of the present invention include reducing odor, reducing iodine content and rejecting epiphytes, which is beneficial to cost-effective mass production of a high-quality additive.

The novel 'Brominata' of the present invention is anatomically distinguished from the parent plant in a number of ways and was accomplished by a vegetative breeding program to increase bromoform concentration.

BRIEF SUMMARY OF THE INVENTION

According to one aspect, in the present invention, we have discovered, isolated and grown a novel and distinct *Asparagopsis taxiformis* named 'Brominata' with a higher bromoform concentration, lower odor, lower iodine content and higher purity than the parent plants. The features of 'Brominata' are suitable for culture in large-scale algaculture and for use as a cattle feed additive. This 'Brominata' was developed in 3 phases in Kailua-Kona, Hi., USA:

i) Collection of parent plant;

ii) Manipulation, dissection and growth in a "seed bank" room; and iii) Selection of appropriate material from seed stock.

For the step of collecting the parent plant, wild type *Asparagopsis taxiformis* is collected from algal turfs or as free-floating algae in the wild. For the step of manipulation, dissection and growth in a "seed bank" room, samples are observed and manipulated under a dissecting microscope to isolate, to the extent possible, clean filaments of *Asparagopsis taxiformis* and separate out contaminants (e.g., epiphytes, other algae, marine animals, contaminated or unhealthy *Asparagopsis taxiformis*). Tiny branches are cut from the mother plant and placed in sterile well plates with seawater, each well containing 360 μL of water. These samples are maintained in a "seed bank" (a room with controlled temperature conditions, contamination protection and carefully-calibrated light with 12-hour photoperiod daily). Cultures are regularly examined. When more than doubled in size, they are stepped-up to larger sterile well plates and then again to sterilized test tubes with 30 ml seawater.

For the step of selecting appropriate material from seed stock, after seven days in test tubes, material that is growing rapidly and, under magnification, appears completely free of epiphytes and fouling organisms is promoted to 250 ml flasks and moved to the nursery. An additional selection step may include selecting for promotion organisms exhibiting larger than usual gland cells. From material that has not achieved those standards, tips representing new growth are cut from the material, which is returned to the smallest sterile well plates with seawater, beginning the process again. The light levels and temperature within the seed bank are controlled to 10-100 μE and 65-85° F. to ensure sustained growth. The growing medium is supplemented with micronutrients in the form of F/2 medium.

As in the seedbank, material in the nursery is grown in an environment that is carefully maintained, including control of light (intensity, spectrum, photoperiod), temperature, micronutrients and aeration. Furthermore, flasks are aerated to ensure algae have sufficient supply of $CO_2$ for photosynthesis and $O_2$ for respiration. Aeration also promotes movement of biomass (beneficial to ensure access to light and prevent formation of biofilm).

Throughout the process, either deep sea water or artificial seawater is used depending on the needs of the plant. Artificial seawater is typically used early in the process when plants are most vulnerable to pests and diseases, and deep seawater later in the process because it contains a rich mix of nutrients that speed plant growth.

DETAILED BOTANICAL DESCRIPTION

Figure 1:
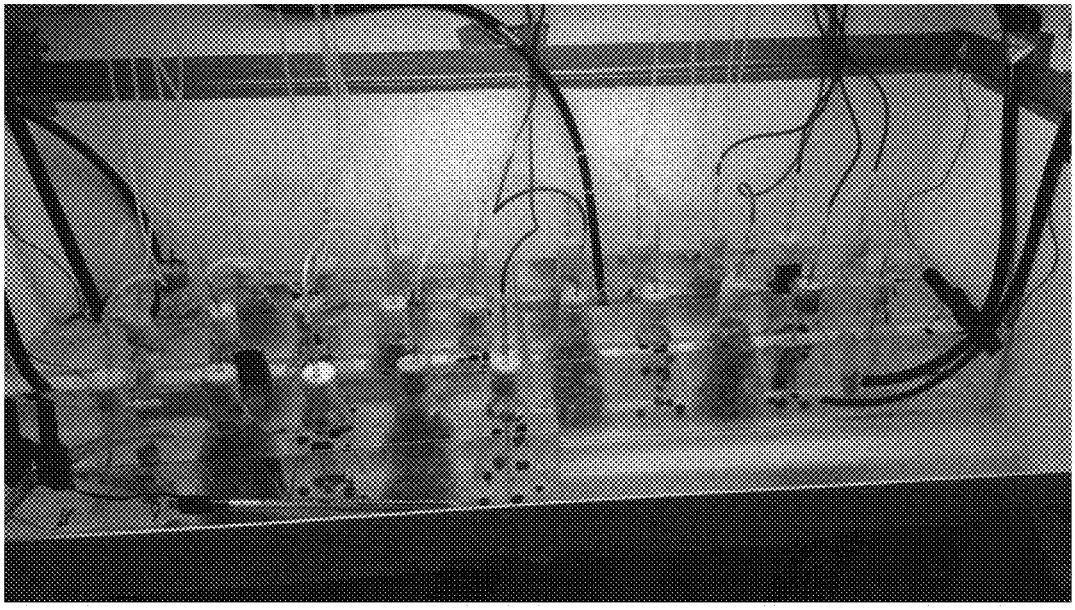
FIG. 1 shows the growth of 'Brominata' tetrasporophyte material in the nursery as the "filamentous" form (uniform red material in the Erlenmeyer flasks, and the "puffball" form as the darker red floating spheres.
Figure 2:
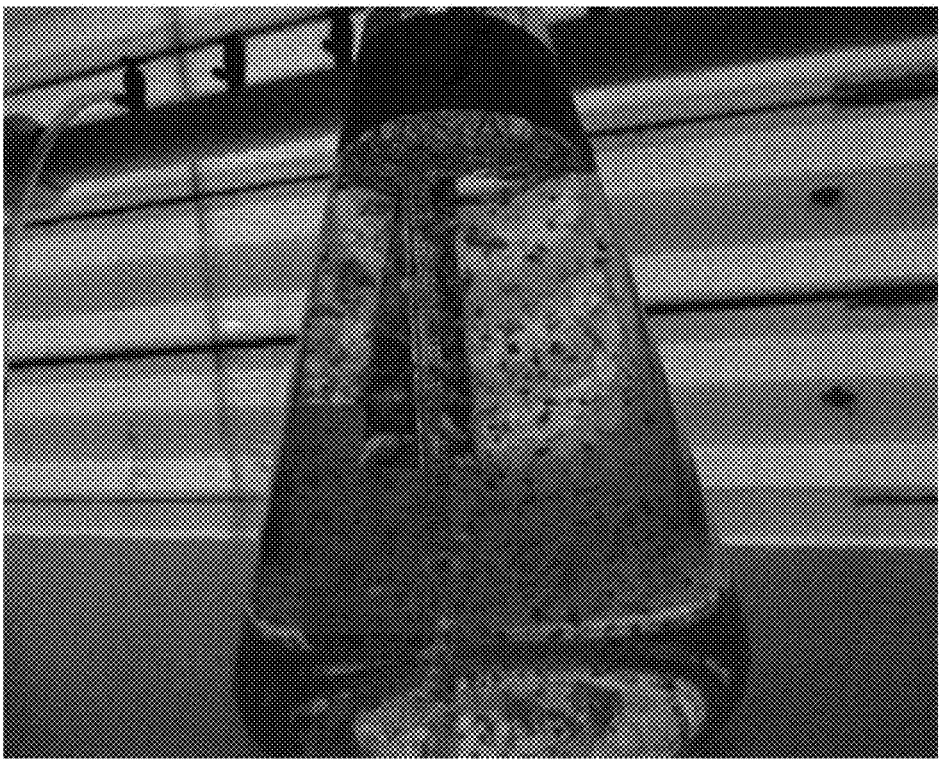
FIG. 2 shows a closeup of the non-filamentous 'Brominata' tetrasporophyte form.
Figure 3:
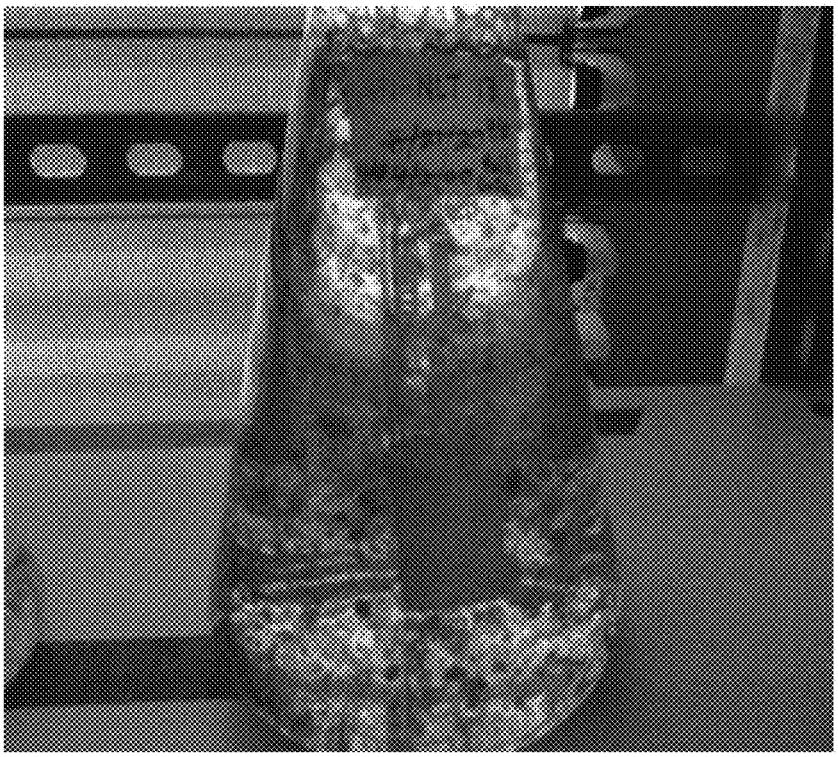
FIG. 3 shows another closeup of the non-filamentous 'Brominata' tetrasporophyte form.
Figure 4:
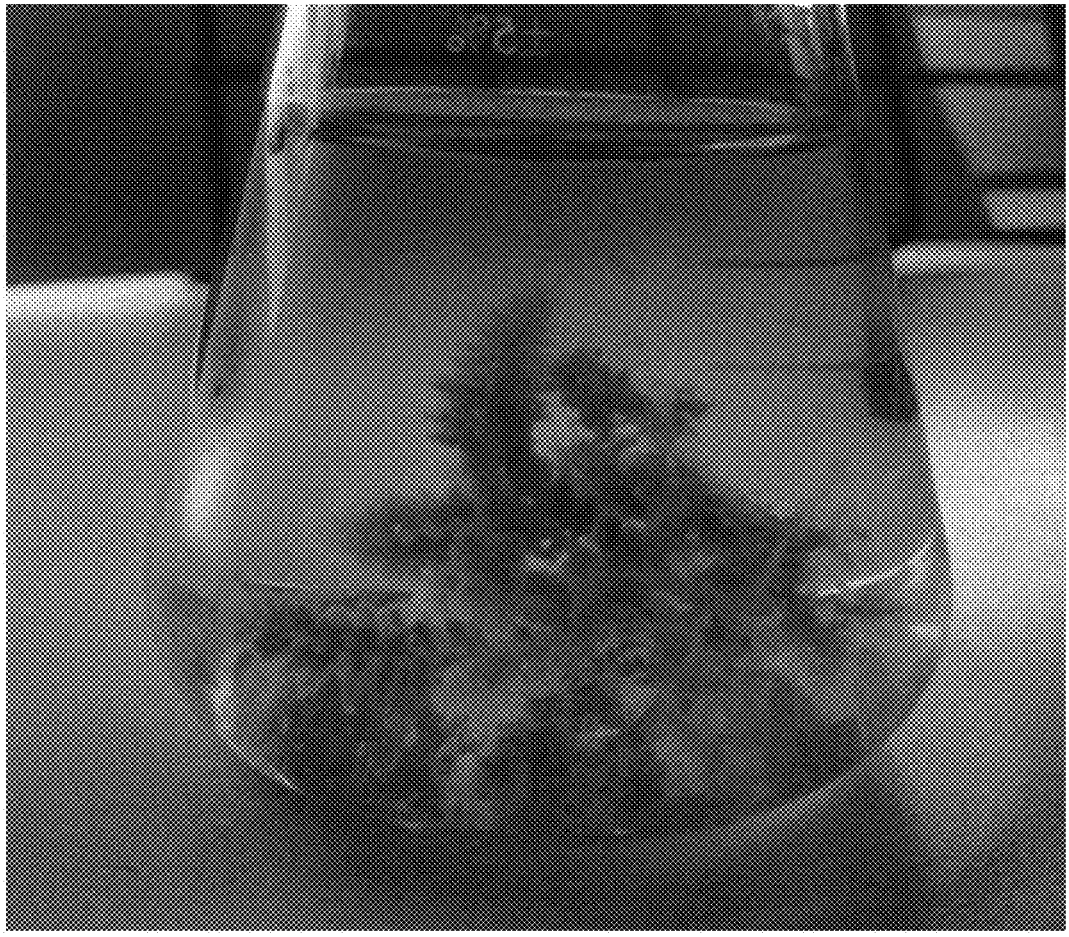
FIG. 4 shows naturally occurring gametophytes (the parent plant). Note the anatomical differences between 'Brominata' tetrasporophytes and parent gametophytes, in terms of the size and shape of the plants.
Figure 5:
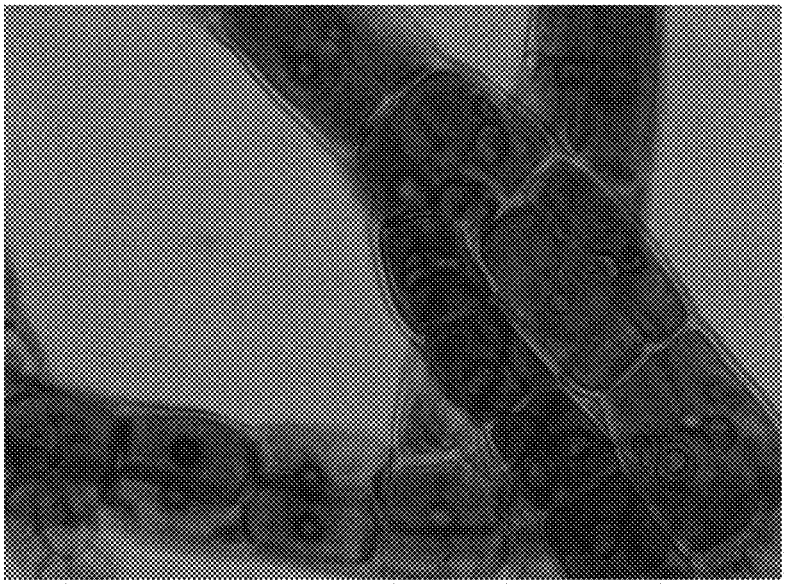
FIG. 5 shows a photomicrograph of 'Brominata' tetrasporophyte material growing in the laboratory. Note the unusually large gland cells (the orange/black dots). The gland cells are what contains the active ingredient (bromoform). Large gland cells indicate an unusually high concentration of bromoform.
Figure 6:
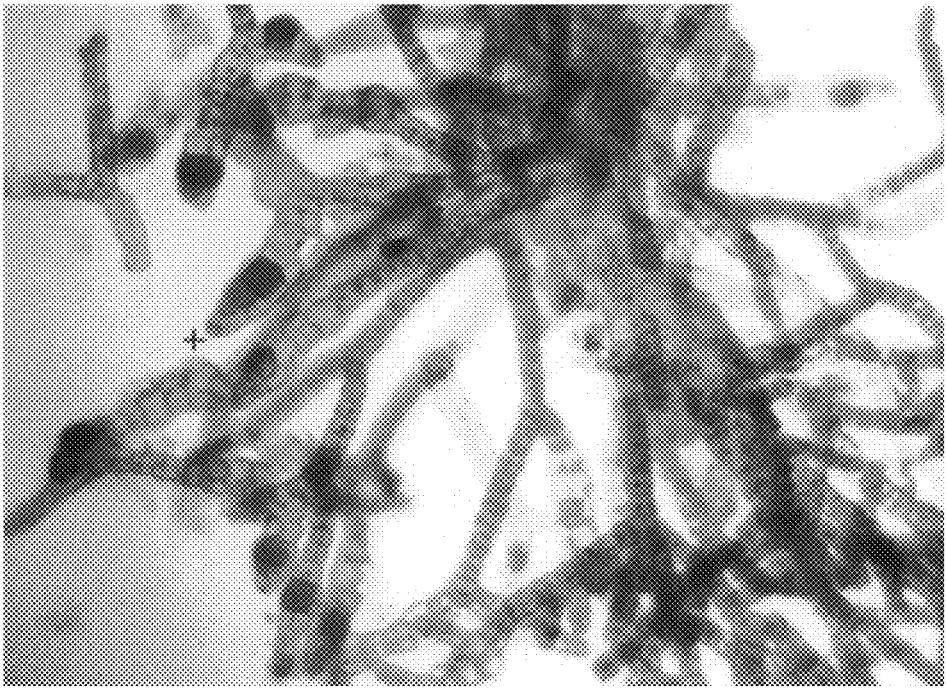
FIG. 6 is a photomicrograph of 'Brominata' tetrasporophytes creating undesired spores. Spores detract energy from growth and bromoform synthesis.
Figure 7:
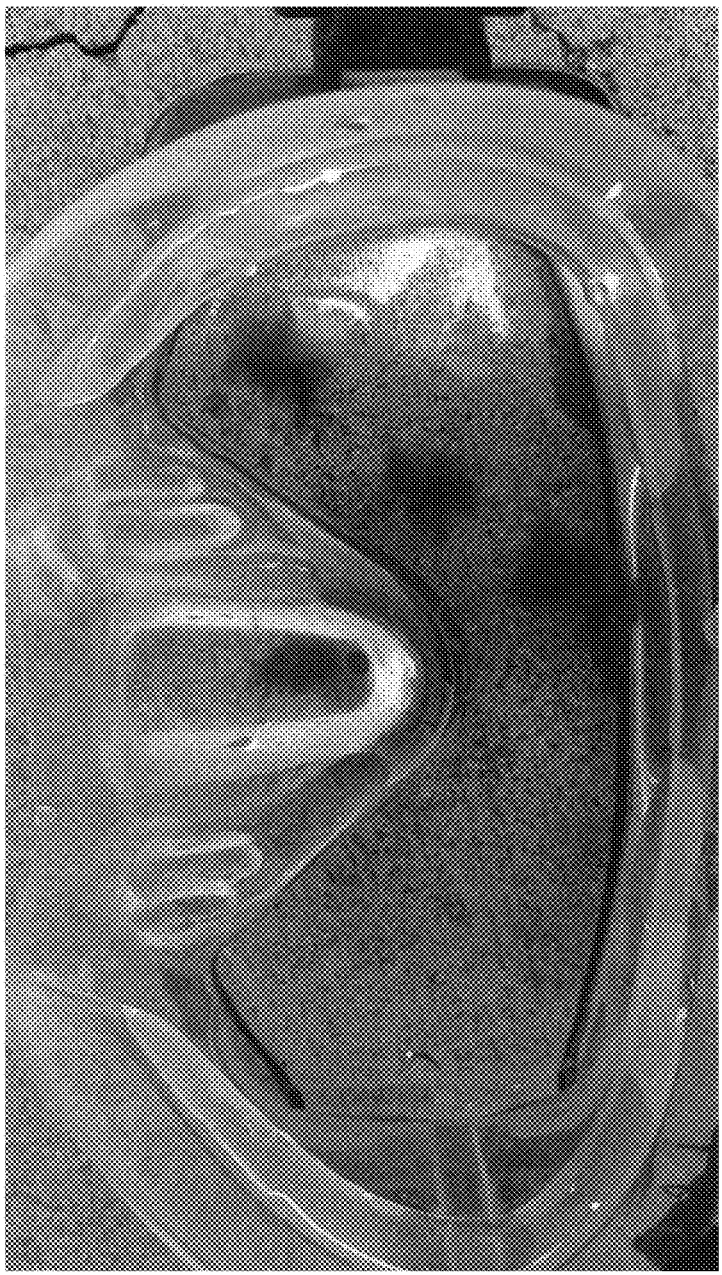
FIG. 7 is a photo of wild 'Brominata' tetrasporophytes used as starting material for the breeding and cultivation program.

The present invention comprises the novel and distinct 'Brominata' that is created through the aforementioned collection, manipulation, dissection and selection process.

The resulting 'Brominata' plant is a small red alga comprising microscopic branched chains of cells. Unlike the gametophyte form, where cells have differentiated functions (holdfast, stem, blades etc.), the cells in the tetrasporophyte are not highly differentiated. Instead, each cluster of four cells is roughly equivalent and these clusters string together into long chains. The color ranges from pale pink to red to dark cherry.

Each branch contains gland cells where the bromoform is stored. These gland cells are a dark red to brown in color, with deeper color indicating higher bromoform concentration.

'Brominata' is not rooted, but rather free-floating in water. 'Brominata' obtains all its organic and inorganic nutrients from the water and can live in this state indefinitely, unlike the parent plant.

'Brominata' is anatomically distinguished from others by stasis in the third phase, the 'Brominata' tetrasporophyte phase. Wild *Asparagopsis taxiformis* typically follows a progression through three life stages (gametophyte, carposporophyte and tetrasporophyte). 'Brominata' is static in the tetrasporophyte phase. This is particularly beneficial because one hundred (100%) percent of tetrasporophytes create high levels of bromoform, in contrast to just fifty (50%) percent of gametophytes synthesize meaningful amounts of bromoform. In addition, since the present tetrasporophytes are static in phase they are not producing spores. This means they can devote all of their energy to growth, which is correlated with even higher bromoform concentrations.

Furthermore, 'Brominata' is special even within the tetrasporophyte class. While tetrasporophytes, left to their own devices, devolve from "puffballs" into a filamentous form, the present 'Brominata' tetrasporophytes can be maintained in the "puffball" phase. This is advantageous because the 'Brominata' "puffball" form grows faster than the filamentous form. Again, this may be correlated with higher bromoform concentrations.

'Brominata' is not limited to the "puffballs" form but also encompasses the larger, "cotton ball" form and the longer "filamentous" chains.

Given these anatomical differences, the composition of 'Brominata' is materially different to the parent *Asparagopsis taxiformis*. In particular, 'Brominata' has a much higher bromoform to iodine ratio than the parent *Asparagopsis taxiformis*. Without wishing to be bound to a particular theory, it is believed that the lower iodine levels may, in part, be due to high rates of bromoform synthesis and storage displacing iodine in gland cells (where bromoform is stored), as outlined in Table 1 below:

TABLE 1

Comparison of Bromoform and Iodine content in Asparagopsis taxiformis Gametophyte and 'Brominata' Tetrasporophyte

| Sample | Type of material | Iodine (ppm) | Average bromoform (μg/g) | Bromoform to iodine ratio (μg/g: ppm) |
|---|---|---|---|---|
| AT Beef Bag 1 | Gametophyte | 2265 | 7961 | 3.5 |
| AT Beef Bag 15 | Gametophyte | 2336 | 7371 | 3.2 |
| AT Beef Bag 21 | Gametophyte | 2201 | 8192 | 3.7 |
| Wild Tetrasporophyte | Tetrasporophyte | * >67.4 | **500-1500 | * <<22.3 |
| 'Brominata' | Tetrasporophyte | 67.4 | 9600 | 142.4 |

* Because we established that there is a strong inverse correlation between bromoform and iodine content in the types of algal biomass studied here, we assert that the iodine content of the Asparagopsis tax iformis tetrasporophyte assayed here for bromoform is significantly higher than in 'Brominata'.
**This is the typical range of bromoform that we expect would be found in wild harvested analogous Asparagopsis spp.

In addition, it is suitable for culture in vitro under illuminated and natural light environments typical of mass production, as described below.

Other distinguishing features include the taste and odor of the plant. While naturally occurring, gametophytes tend to be malodorous, 'Brominata' tetrasporophytes have low odor. This is beneficial, since low-odor food tends to be more palatable.

*Asparagopsis taxiformis* tends to grow as epiphytes. 'Brominata' is distinct because it grows as an isolated algae species. This has a number of advantages for algal culture, including the fact that all nutrients go towards the growth of *Asparagopsis taxiformis* rather than competitive species and increased product purity.

Nevertheless, 'Brominata' is a fragile species, highly vulnerable to pests, diseases and competitive algae. The introduction of pests or contaminants may be prevented through a variety of mechanisms such as, but not limited to: purification cycles, maintaining positive air pressure in the flasks, using stoppers on flasks to prevent ingress of materials, wearing lab coats and using shoe dips to prevent pests or contaminants entering the lab. Furthermore, 'Brominata' has low resistance to shipping or environmental changes. It can be killed or bleached by changes in temperature or light intensity. Given this sensitivity, the plant is grown under controlled environmental conditions. Light is provided by incandescent, halogen, LED, fluorescent, high intensity discharge, metal halide, high pressure sodium or other suitable lights and maintained at 10-100 μE in the seed bank and nursery using 60-80% Blue Pearl shade cloth. Suitably filtered and controlled natural light, if available, properly filtered, and of sufficient duration may also be used as the main, light source, or as a supplement or complement to the artificial light sources named herein, but tightly controlled artificially supplied light is preferable. The photoperiod is maintained at 12 hours per day to prevent spore formation. Within the nursery, flasks are aerated to ensure algae have sufficient supply of $CO_2$ for photosynthesis and $O_2$ for respiration. Aeration also serves to promote movement of biomass. This ensures all algae have access to light, reduces the formation of biofilm, and prevents clumping of algae, which can create an anoxic environment where bacteria or contaminants grow. Nutrients are provided through F/2 medium in approximately the concentrations depicted in Table 2. Temperature is maintained at 65-85° F. (between about 18 and 30° Celsius) throughout the day.

TABLE 2

Concentrations of Nutrients in the F/2 Medium

| Nutrient | Concentration (ml/L) |
|---|---|
| Nitrogen | 6.998 |
| Phosphate | 1.500 |
| Vitamin B1 | 0.053 |
| Vitamin B12 | Trace |
| Biotin | Trace |
| Iron* | 0.735 |
| Manganese* | 0.026 |
| Cobalt* | 0.002 |
| Zinc* | 0.003 |
| Copper* | 0.001 |
| Molybdate* | 0.001 |

*Only added for artificial seawater, not deep seawater

Grown under these conditions, 'Brominata' is a stable and uniform culture that is distinct from the parent plant. Wild type *Asparagopsis taxiformis* has unpleasant odor, high iodine content, epiphytic nature, and lack of capacity, especially in male specimens, to synthesize material concentrations of the halogenated compounds. The present variety has higher bromoform content, lower odor, lower iodine, an absence of epiphytes and is static in the tetrasporophyte phase. These anatomically distinguishing features beneficial to cost-effective mass production of a high-quality additive.

Photomicrographs were taken of wild type *Asparagopsis taxiformis* samples and 'Brominata' samples. The samples were prepared by carefully spreading a small pinch of alga on a microscope slide with tweezers, adding 2 drops of seawater, and carefully adding a cover slide. The slide was immediately placed on the compound microscope or dissecting scope. On the compound scope, the slide was viewed through a 20× or 40× objective with a 10× eyepiece lens for a final magnification of ×200 or ×400 with an illumination setting of 4. On the dissecting microscope, the slide was viewed at a magnification of 2.5× with a 10× eyepiece lens for a final magnification of ×25. The microscope used was an Olympus CX43 with the UPlanFLN objectives. The microscope has six filters including a BF (bright field), 2×, DF, Ph3, Ph2, Ph1. The dissecting scope was an Olympus SZX16 with an SDF PLAPO 1×PF objective. The filters on the microscope included BF, PO, Oblique, DF. The camera attached to the microscope is an Olympus SC 180 camera with U-TV 0.5× camera adapter. The computer software used to take microscope photos was a cellSens Entry. Photos were saved as JPEG.

Under this brightfield photomicroscopy, 'Brominata' exhibits a much darker green signal. In a typical experiment, the following color values were observed: The photomicrographs were imported into Photoshop as JPEG files. The scale was a 397×459 pixel image at 72 pixels/inch. 5×5 pixel average color samples were obtained in Adobe Photoshop from the middle of a cell as shown approximately by the black circles in the respective images. A 0.5×0.5 inch patch was created from the RGB values of the samples of the wild type *Asparagopsis taxiformis* and 'Brominata' images and compared with The Royal Horticultural Society Colour Charts Edition V.

Figure 12:
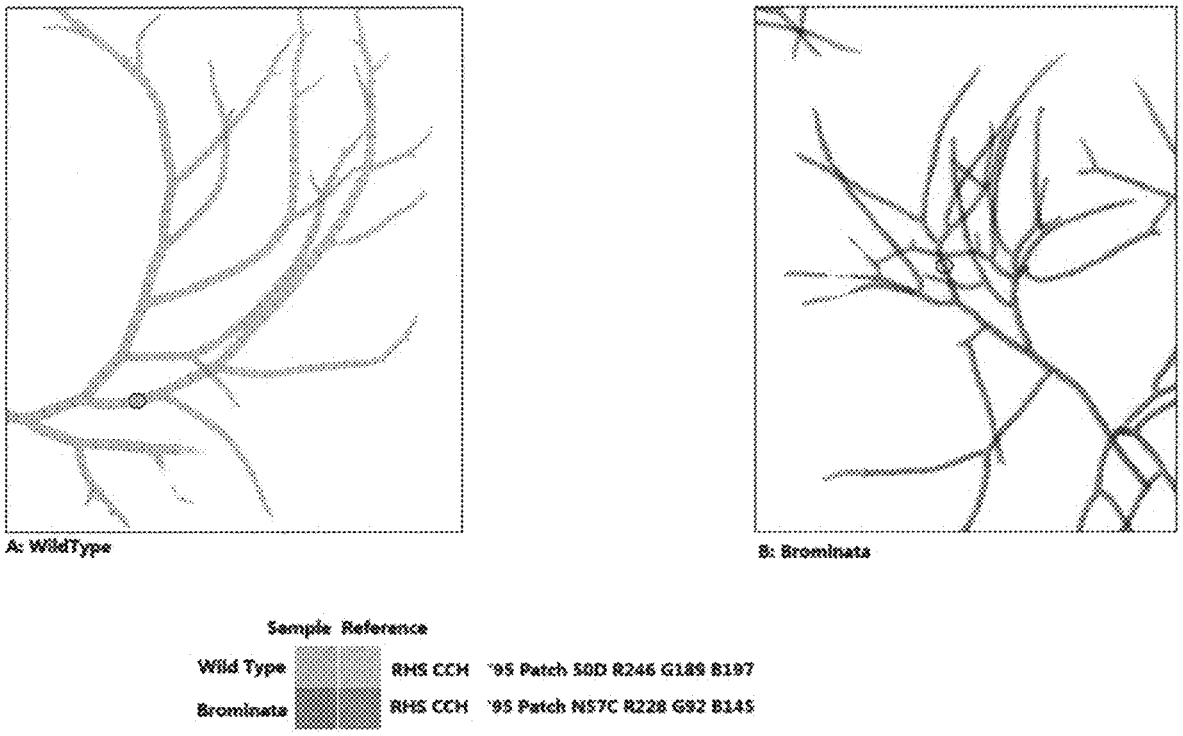
FIG. 12 are pictures showing a comparison of branching in wild type *Asparagopsis taxiformis* Panel A (left) and 'Brominata' Panel B (right). The wild type *Asparagopsis taxiformis* reference color patch is from the Yellow-Red group of The Royal Horticultural Society Colour Charts Edition V, while the 'Brominata' reference color patch is from the Purple-Blue group of the of The Royal Horticultural Society Colour Charts Edition V. The sample patches to the left of the reference patches were derived by sampling an average color of a 5×5 pixel region as shown by the black circle on the respective images.

The wild type *Asparagopsis taxiformis* 'sample patch most closely matched patch 50D from the Yellow-Red set, while the 'Brominata' derived patch most closely matched patch N57C from the Purple-Blue group. Reference color patches were created from the published RGB values of The R.H.S. color chart patches and juxtaposed against the corresponding sample patches as seen in FIG. 12. The 'Brominata' reference color patch had a much lower "G" signal as compared to the wild type *Asparagopsis taxiformis* reference patch and having modestly lower "R" and "B" values as compared to the wild type *Asparagopsis taxiformis* reference patch as well.

Figure 8:
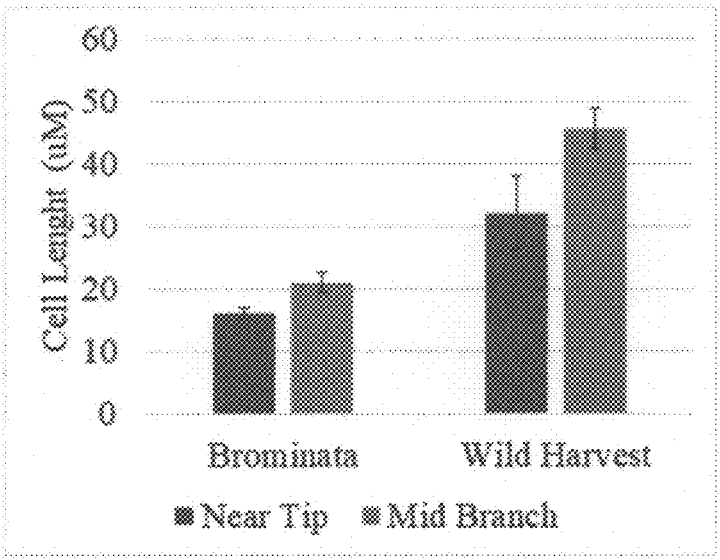
FIG. 8 is a graph showing cell length difference between 'Brominata' and wild type *Asparagopsis taxiformis*.
Figure 9:
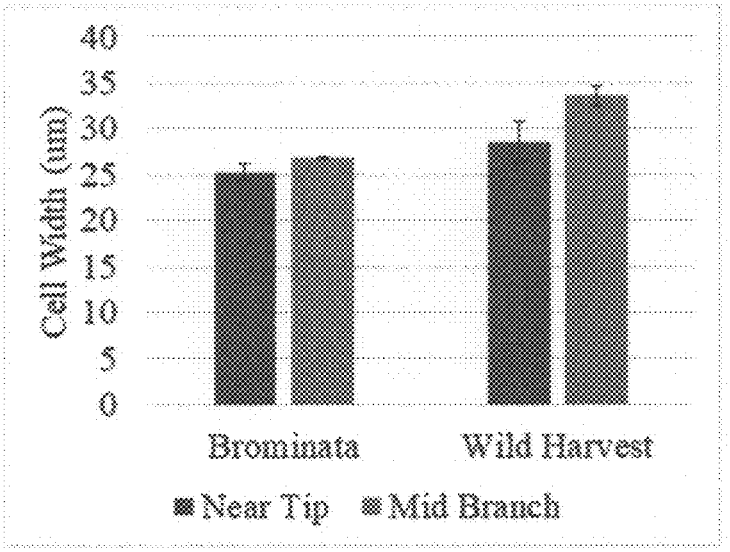
FIG. 9 is a graph showing cell width difference between 'Brominata' and wild type *Asparagopsis taxiformis*.
Figure 10:
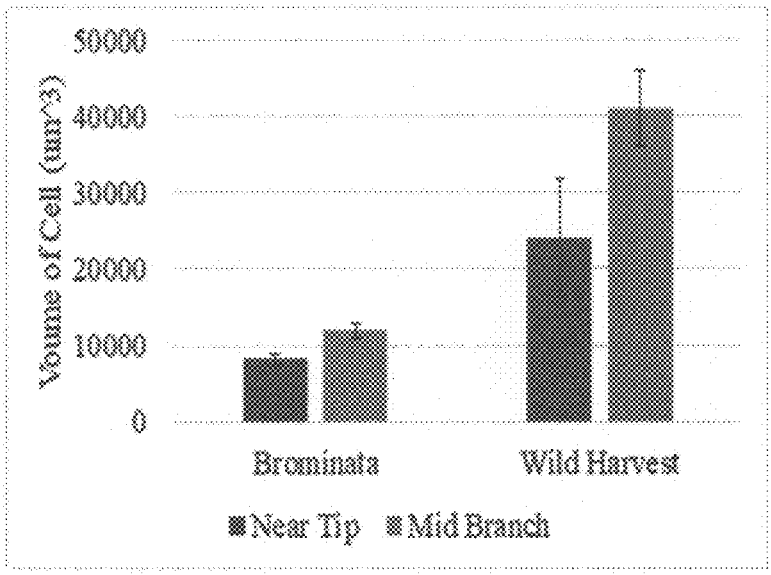
FIG. 10 is a graph showing a volume comparison of gland cells from 'Brominata' and wild type *Asparagopsis taxiformis*.
Figure 11:
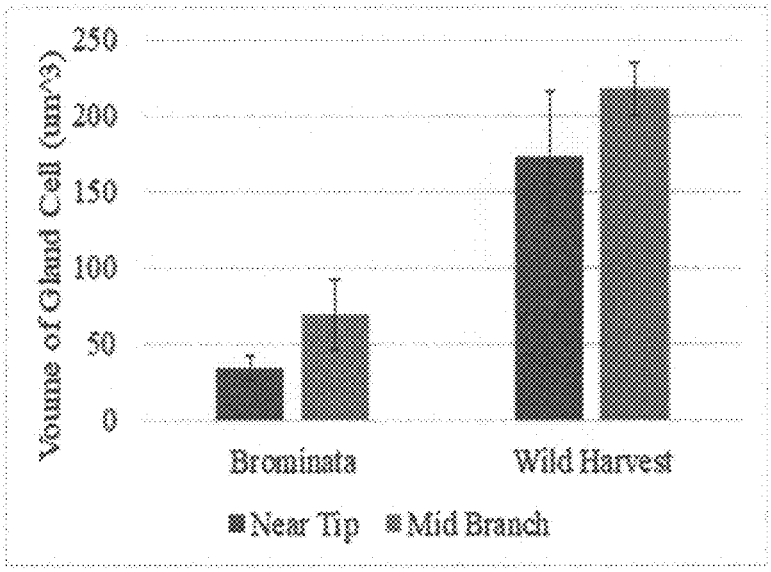
FIG. 11 is a graph showing a volume comparison of gland cells from 'Brominata' and wild type *Asparagopsis taxiformis*.
Figure 13:
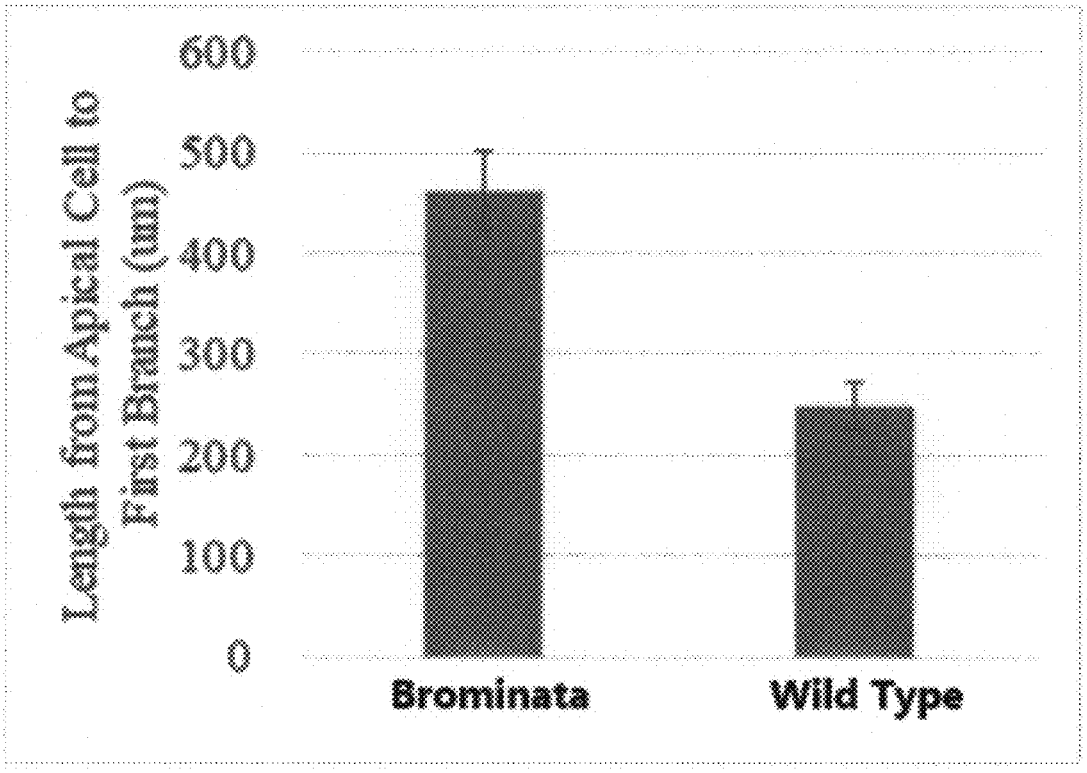
FIG. 13 is a graph showing quantification of branching morphology between 'Brominata' and wild type *Asparagopsis taxiformis*.

Quantitative morphology: Wild-type *Asparagopsis taxiformis* and 'Brominata' were also compared quantitatively with regard to cell length and width, the volume of the cell to the gland cell, the branching pattern, and the holdfast. Using the ImageJ software, the length and width of the cells were measured 5, 7, and 9 cells distance from the apical cell. The results are reported in FIGS. 8 and 9. The results show that there is a significant difference in the cell length between 'Brominata' and the wild type *Asparagopsis taxiformis*. A review of publications on *Asparagopsis taxiformis* found that the data collected from the wild harvest material with an average length of 45 μm at the mid-branch, matches that of other wild harvested material, which ranged from 40-65 μm) (Chualáin et al. 2004). The length of the cells in 'Brominata' averaged a length of 20 μm at the mid-branch was shorter than the wild type *Asparagopsis taxiformis*. Throughout the body of 'Brominata', the cell and gland cell size were significantly smaller as shown in FIGS. 10-11. Branching analyses are shown in FIGS. 12-13. The analysis shows that 'Brominata' exhibits an average of around 462 μm distance from apical cell to the first branch point versus about 248 μm for the wild type *Asparagopsis taxiformis*.

The invention claimed is:

1. A new and distinct variety of *Asparagopsis taxiformis* algae named 'Brominata', substantially as herein illustrated and described.

* * * * *